(12) United States Patent
Robert et al.

(10) Patent No.: US 10,835,275 B2
(45) Date of Patent: Nov. 17, 2020

(54) APPARATUS FOR REMOVABLY RECEIVING AN END EFFECTOR FOR PERFORMING SURGICAL OPERATIONS

(71) Applicant: Titan Medical Inc., Toronto (CA)

(72) Inventors: Rene Robert, East Greenwich, RI (US); Jonathan Hess Hills, Sunnyvale, CA (US)

(73) Assignee: TITAN MEDICAL INC., Toronto (CA)

(*) Notice: Subject to any disclaimer, the term of this patent is extended or adjusted under 35 U.S.C. 154(b) by 180 days.

(21) Appl. No.: 16/084,368

(22) PCT Filed: Mar. 15, 2017

(86) PCT No.: PCT/CA2017/000056
§ 371 (c)(1),
(2) Date: Sep. 12, 2018

(87) PCT Pub. No.: WO2017/156618
PCT Pub. Date: Sep. 21, 2017

(65) Prior Publication Data
US 2019/0069918 A1 Mar. 7, 2019

Related U.S. Application Data

(60) Provisional application No. 62/308,296, filed on Mar. 15, 2016.

(51) Int. Cl.
*A61B 17/00* (2006.01)
*A61B 17/29* (2006.01)
(Continued)

(52) U.S. Cl.
CPC .......... *A61B 17/2909* (2013.01); *A61B 34/30* (2016.02); *A61B 2017/00314* (2013.01);
(Continued)

(58) Field of Classification Search
CPC ........ A61B 2017/003; A61B 2017/294; A61B 2017/2902; A61B 2017/292; A61B 2018/00172; A61B 1/0053
See application file for complete search history.

(56) References Cited

U.S. PATENT DOCUMENTS 5,522,788 A 6/1996 Kuzmak
8,573,465 B2 11/2013 Shelton
(Continued)

FOREIGN PATENT DOCUMENTS

WO  WO 99/15089     4/1999
WO  WO 2014/201538  12/2014
(Continued)

OTHER PUBLICATIONS

International Search Report and Written Opinion in International Application No. PCT/CA2017/000056, dated Jun. 19, 2017, in 8 pages.

*Primary Examiner* — Wade Miles
*Assistant Examiner* — Mohammed S Adam

(57) ABSTRACT

A surgical instrument apparatus for removably receiving an end effector coupled to an elongate control link for actuating the end effector to perform surgical operations is disclosed. The apparatus includes an actuator housing and an elongate shaft extending from the actuator housing and having a bore for receiving the control link. The apparatus also includes an actuator mounted within the actuator housing and includes a clamp aperture disposed to receive the control link while the clamp aperture is being urged into an undamped state by an opening force, the clamp aperture being operably configured to move between the undamped state and a clamped state in response to the opening force being released, the aperture in the clamped state being operable to restrain the control link (Continued)

within the actuator for movement in a longitudinal direction substantially aligned with the elongate shaft.

12 Claims, 3 Drawing Sheets

(51) Int. Cl.
*A61B 34/30* (2016.01)
*A61B 90/00* (2016.01)
*A61B 18/00* (2006.01)

(52) U.S. Cl.
CPC ............... *A61B 2017/00464* (2013.01); *A61B 2017/292* (2013.01); *A61B 2017/2944* (2013.01); *A61B 2017/2946* (2013.01); *A61B 2018/00172* (2013.01); *A61B 2034/302* (2016.02); *A61B 2090/08021* (2016.02)

(56) References Cited

U.S. PATENT DOCUMENTS

| | | | | |
|---|---|---|---|---|
| 2005/0080440 A1* | 4/2005 | Durgin | ............... | A61B 17/1285 606/157 |
| 2009/0171147 A1* | 7/2009 | Lee | .................. | A61B 17/32002 600/104 |

FOREIGN PATENT DOCUMENTS

| | | |
|---|---|---|
| WO | WO 2016/090459 | 6/2016 |
| WO | WO 2017/156618 | 9/2017 |

\* cited by examiner

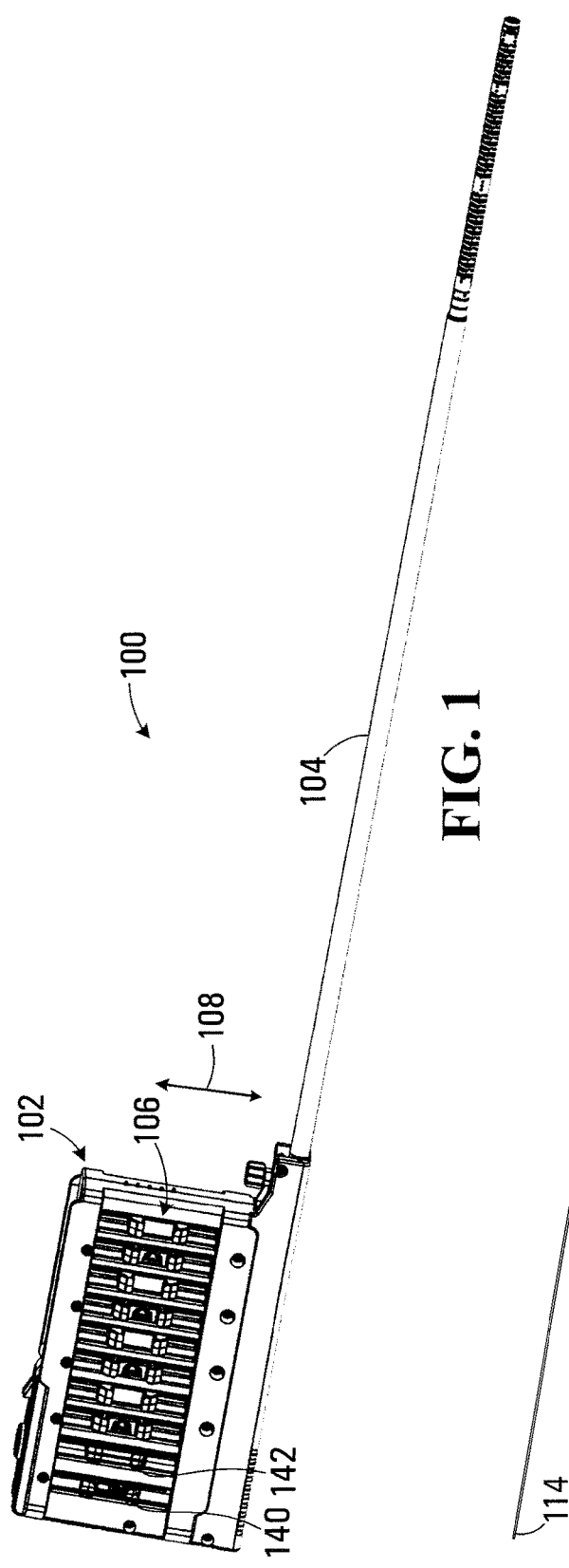
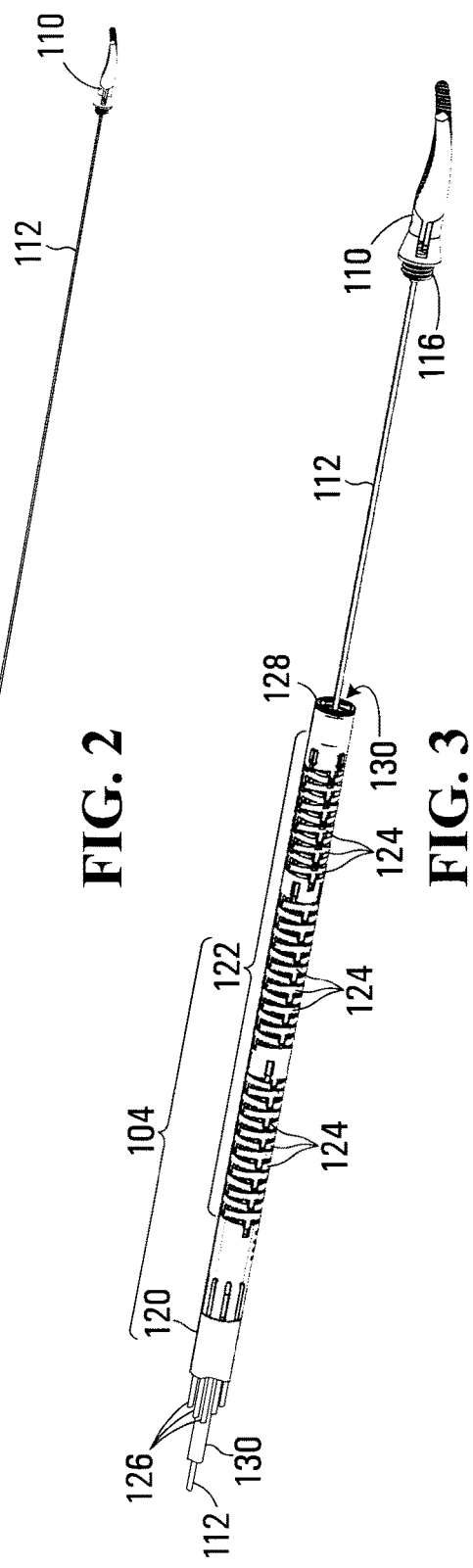
FIG. 1
FIG. 2
FIG. 3

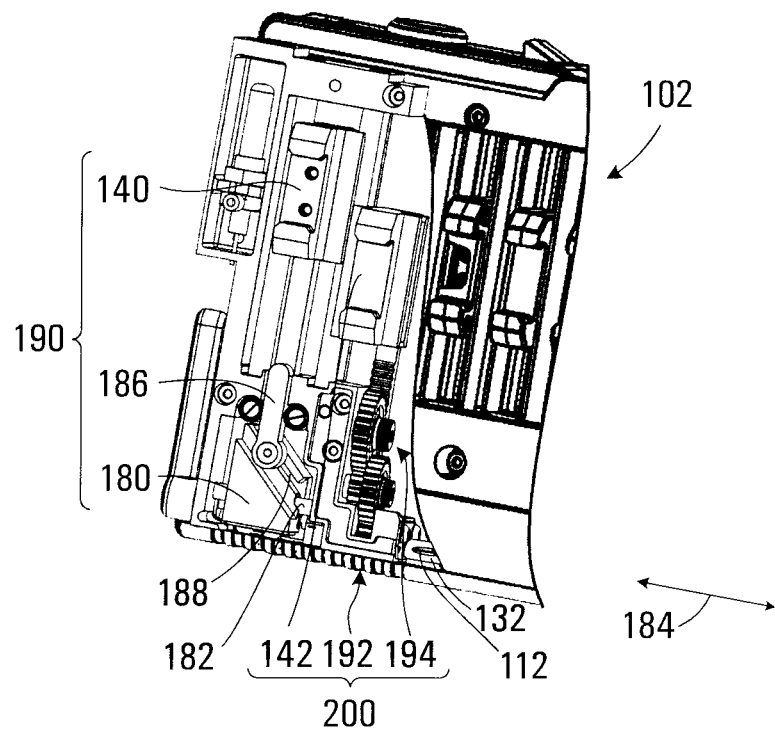
FIG. 4
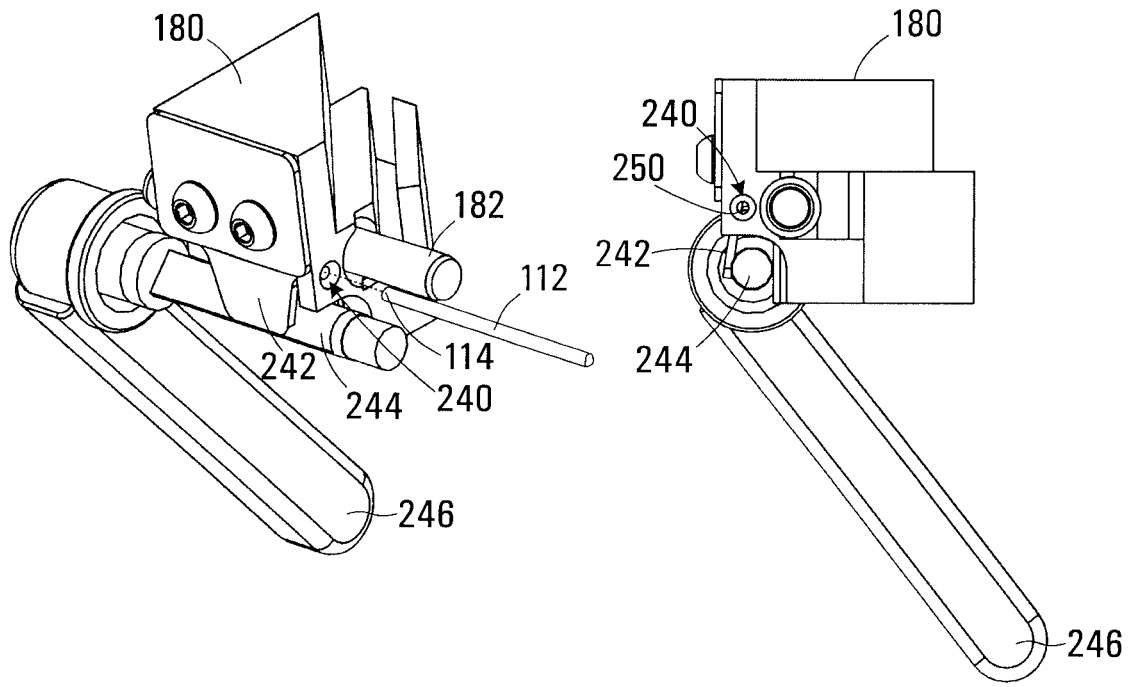
FIG. 5  FIG. 6

APPARATUS FOR REMOVABLY RECEIVING AN END EFFECTOR FOR PERFORMING SURGICAL OPERATIONS

CROSS-REFERENCE TO RELATED APPLICATION

This application is a U.S. National Phase Application under 35 U.S.C. 371 of International Application No. PCT/CA2017/000056 filed on Mar. 15, 2017, and published as WO 2017/156618 A1 on Sep. 21, 2017, which claims priority to U.S. Provisional Application No. 62/308,296, filed on Mar. 15, 2016. The entire disclosures of all of the above applications are incorporated herein by reference.

BACKGROUND

1. Field

This disclosure relates generally to surgical instruments and more particularly to a surgical instrument for laparoscopic or robotic surgery.

2. Description of Related Art

Robotic surgical systems commonly employ one or more instruments assemblies that are manipulated by a robotic system to perform surgical tasks. Each instrument is generally equipped with an end effector, such as a surgical scissor, forceps, dissector, or other end effector for performing specific operations. Commonly, the instrument is configured with a specific end effector and changing the end effector may require some disassembly of the instrument.

SUMMARY

In accordance with one disclosed aspect there is provided a surgical instrument apparatus for removably receiving an end effector coupled to an elongate control link for actuating the end effector to perform surgical operations. The apparatus includes an actuator housing and an elongate shaft extending from the actuator housing and having a bore for receiving the control link. The apparatus also includes an actuator mounted within the actuator housing and includes a clamp aperture disposed to receive the control link while the clamp aperture is being urged into an unclamped state by an opening force, the clamp aperture being operably configured to move between the unclamped state and a clamped state in response to the opening force being released, the aperture in the clamped state being operable to restrain the control link within the actuator for movement in a longitudinal direction substantially aligned with the elongate shaft.

The clamp aperture may include a channel for receiving the control link, and a clamp plate disposed to engage and exert a clamping force on the control link when the aperture is in the clamped state, the clamp plate being operable to resiliently deform in response to the opening force causing the clamp plate to disengage from the control link.

The clamp plate may be mounted to the actuator at a location distal to the channel and may include a cantilevered length extending over the channel, the cantilevered length of the clamp plate being configured to provide the resilient deformation.

The cantilevered length may include a first cantilevered length extending beyond the channel, and a second cantilevered length in offset relation to the first cantilevered length and extending back over the channel, the first and second cantilevered lengths configured to provide the resilient deformation.

The clamp plate may be mounted to the actuator using a compliant mounting that permits further resilient deflection of the clamp plate about the compliant mounting.

The channel may include a material treated to increase friction for preventing slippage of the control link within the channel when the aperture is in the clamped state.

The apparatus may include a clamp lever operable to provide the opening force when in an open position.

The lever in the open position may protrude from the actuator housing and prevent loading of the surgical instrument into a driver for providing drive forces to the actuator when the clamp aperture is in an open state.

The actuator may include a longitudinally moveable portion housing the clamp aperture, a transversely movable portion for receiving a drive force, and a coupling between the transversely moveable portion and the longitudinally moveable portion, the coupling being operable to convert transverse movement of the transversely moveable portion into longitudinal movement of the longitudinally moveable portion.

The apparatus may include a rotational actuator disposed within the actuator housing, and a torque tube enclosing the elongate control link and extending through the bore of the elongate shaft, the torque tube being coupled to the rotational actuator and having a distal end operable to couple to the end effector for causing rotation of the end effector.

The rotational actuator may include a rotatable portion coupled to the torque tube, and a transversely movable portion for receiving a drive force, and a coupling between the transversely moveable portion and the rotatable portion, the coupling being operable to convert transverse movement of the transversely moveable portion into rotation of the rotatable portion and the torque tube.

The aperture may be located within a longitudinally moveable portion of the actuator and the actuator may further comprise a transversely moveable portion, and a linkage extending between the transversely moveable portion and the longitudinally moveable portion, the linkage being operably configured to translate transverse movement of the transversely moveable portion into longitudinal movement of the longitudinally moveable portion.

In accordance with another disclosed aspect there is provided an end effector for use with the apparatus above, the control link of the end effector having an open end operably configured to be received and clamped within the clamp aperture.

In accordance with another disclosed aspect there is provided a method for removably mounting an end effector in a surgical instrument, the end effector being coupled to an elongate control link for actuating the end effector to perform surgical operations. The method involves receiving the control link within a bore of an elongate shaft extending from an actuator housing of the surgical instrument, the housing including an actuator mounted within the actuator housing for movement in a longitudinal direction substantially aligned with the elongate shaft. The method also involves receiving the control link in a clamp aperture of the actuator while the clamp aperture is being urged into an unclamped state by an opening force, and releasing the opening force to cause the clamp aperture to move between the unclamped state and a clamped state, the aperture in the clamped state being operable to immobilize the control link within the actuator for causing longitudinal movement of the control link.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments,

FIG. 1 is a perspective view of a surgical instrument;

FIG. 2 is a perspective view of an end effector for use with the surgical instrument shown in FIG. 1;

FIG. 3 is a perspective view of a portion of the surgical instrument shown in FIG. 1 receiving the end effector shown in FIG. 2;

FIG. 4 is a cut away perspective view of a portion of an actuator housing of the surgical instrument shown in FIG. 1;

FIG. 5 is front perspective view of a longitudinal actuator and clamp aperture in an open state;

FIG. 6 is a side view of the longitudinal actuator and clamp aperture in the open state;

DETAILED DESCRIPTION

Figure 7:
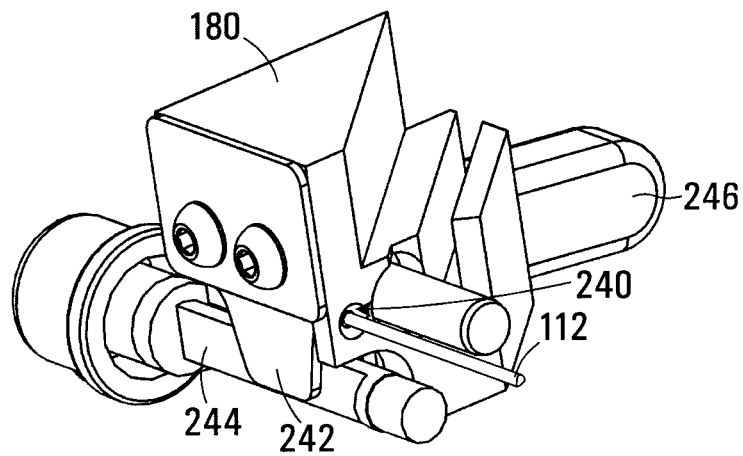
FIG. 7 is a front perspective view of the longitudinal actuator and clamp aperture in a closed state

Referring to FIG. 1, a surgical instrument apparatus in accordance with one disclosed embodiment is shown at 100. The surgical instrument 100 includes an actuator housing 102 and an elongate shaft 104 extending from the actuator housing. The actuator housing 102 houses a plurality of transverse actuators 106 configured for transverse movement in a direction indicated by the arrow 108.

Referring to FIG. 2, a removable end effector for use with the surgical instrument 100 is shown at 110. The end effector 110 is coupled to an elongate control link 112 for actuating the end effector to perform surgical operations. In the example shown, the end effector 110 is a jawed instrument that is opened and closed in response to pushing and pulling movements of a proximate end 114 of the control link 112.

A portion of the surgical instrument 100 is shown in greater detail in FIG. 3 with the end effector 110 being inserted into the instrument. Referring to FIG. 3, in the embodiment shown the shaft 104 includes a rigid portion 120 and an articulated portion 122. The articulated portion 122 includes a plurality of coupled guides 124. A plurality of control links 126 (shown in part only in FIG. 3) extend back from the articulated portion 122 to the actuator housing 102 and are coupled to respective transverse actuators 106 (shown in FIG. 1). In the embodiment shown, the eight transverse actuators 106 that are closest to the elongate shaft 104 are coupled to the plurality of control links 126 while the transverse actuator 140 furthest away from the shaft 104 actuates the control link 112 for operating the end effector 110. The coupled guides 124 are operable to move with respect to each other in response to pushing and/or pulling of the control links 126 causing a distal end 128 of the surgical instrument 100 to assume various positions and orientations. An articulated positioner is described in detail in commonly owned patent application PCT/CA2013/001076 entitled "ARTICULATED TOOL POSITIONER AND SYSTEM EMPLOYING SAME", which is incorporated herein by reference in its entirety. A surgical instrument and actuator housing is described in detail in commonly owned patent application PCT/CA2015/000098 entitled "ACTUATOR AND DRIVE FOR MANIPULATING A TOOL", which is incorporated herein by reference in its entirety.

The shaft 104 has a bore 130 for receiving the control link 112, which is threaded up through the bore toward the actuator housing 102. In this particular embodiment the bore 130 is centrally located and the control link 112 is surrounded by the plurality of control links 126. The control links may be flexible nitinol wires capable of operation in tension or compression without permanent deformation.

In the embodiment shown a torque tube 132 extends along the length of the bore 130 between the actuator housing 102 and the distal end 128 of the shaft 104. The torque tube 132 thus encloses the control link 112 when the end effector 110 is received within the bore 130. The distal end 128 of the torque tube 132 is coupled to the end effector 110 via a threaded connection 116 and is able to rotate within the shaft 104 to cause a corresponding rotation of the end effector. The torque tube 132 is rotated by movement of a transverse actuator 142 in the plurality of transverse actuators 106.

A portion of the actuator housing 102 that houses the end effector actuator and a rotational actuator for causing rotation of the torque tube 132 are shown in cut-away view in FIG. 4.

Referring to FIG. 4, the transverse actuator 140 is coupled to a longitudinally moveable actuator portion 180 to form an end effector actuator 190. The longitudinal actuator 180 is slideably disposed on a shaft 182 for movement in a longitudinal direction indicated by the arrow 184. The longitudinal movement direction 184 is substantially aligned with the shaft 104 (shown in FIG. 1 and FIG. 3). In the embodiment shown the end effector actuator 190 includes a coupling 186 that converts transverse movement of the transverse actuator 140 into longitudinal movement of the longitudinal actuator 180. Transverse movement of the transverse actuator 140 causes corresponding transverse movement of the coupling 186. The coupling 186 engages an angled slot 188 in the longitudinal actuator 180 and causes motion of the longitudinal actuator 180 along the shaft 182.

The surgical instrument 100 includes a rotational actuator 200 including a rotational actuator portion 192 coupled via a coupling 194 to the transverse actuator 142. The torque tube 132 is received within the rotational actuator portion 192 and the coupling 194 converts transverse movement of the transverse actuator 142 into rotational movement for rotating the torque tube 132 and hence the end effector 110. In the embodiment shown the coupling 194 is implemented using a rack-and-pinion mechanism.

The longitudinal actuator 180 is shown in perspective view in FIG. 5 and in side view in FIG. 6. Referring to FIGS. 5 and 6, the longitudinal actuator 180 includes a clamp aperture 240 disposed to receive the proximate end 114 of the control link 112 while the clamp aperture is being urged into an unclamped state by an opening force. In FIGS. 5 and 6 the clamp aperture 240 is shown in an open state ready for receiving the control link 112. The clamp aperture 240 includes a channel 250 for receiving the control link 112. The clamp aperture 240 is operably configured to move between the unclamped state and a clamped state in response to the opening force being released. Referring to FIG. 7, the control link 112 is shown received in the channel 250 of the clamp aperture 240. The clamp aperture 240 is in a clamped state and operable to restrain the control link 112 within the actuator for movement of the longitudinal actuator 180 on the shaft 182 in the longitudinal direction 184.

In the embodiment shown in FIGS. 5-7, the clamp aperture 240 includes a resiliently deformable clamp plate 242, which is compliantly mounted on the longitudinal actuator 180 and disposed to engage and exert a clamping force on the control link 112 when the aperture 240 is in the clamped state. An eccentric pin 244 actuated by a clamp lever 246 provides an opening force that causes the clamp plate 242 to resiliently deform (as best shown in FIG. 6) causing the clamp plate to disengage from the channel 250 to allow the control link 112 to be inserted. When the opening force is released by moving the clamp lever 246 to position shown in FIG. 7, the clamp plate 242 is resiliently urged into contact with the control link 112 within the channel 250. In the clamped state, a clamping force is thus provided passively by the clamp plate 242 and there is no tension on the clamp lever 246.

Figure 8:
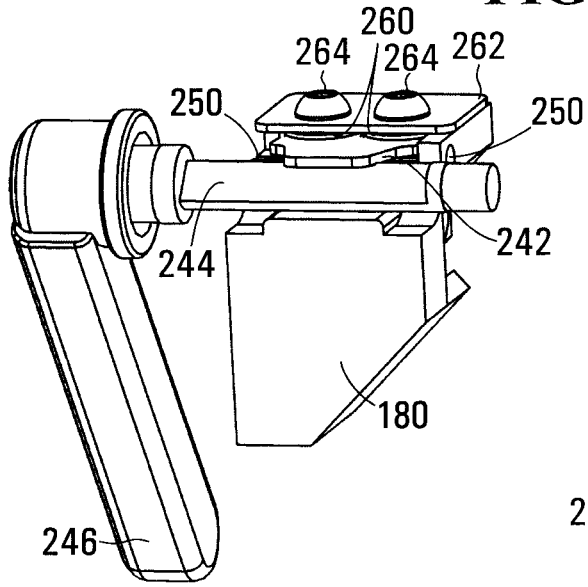
FIG. 8 is a side perspective view of the longitudinal actuator shown in FIGS. 5-7.

Referring to FIG. 8, the clamp plate 242 is mounted to the longitudinal actuator 180 at a location distal to the channel 250 and includes a cantilevered length extending over the channel. The cantilevered length of the clamp plate is configured to provide the resilient deformation. Additionally, the clamp plate 242 is mounted to the longitudinal actuator 180 using a compliant mounting provided in this embodiment by Bellville washers 260. The Bellville washers 260 are sandwiched between a mounting plate 262 and the clamp plate 242 and the mounting plate is held by a pair of screws 264 that are received in threaded holes (not shown) within the longitudinal actuator 180. The Bellville washers 260 permit the clamp plate 242 to disengage from the channel 250 when an opening force is provided by the clamp lever 246 and the eccentric pin 244. The retaining force provided by the clamp plate 242 may thus be partly due to the resilience of the clamp plate 242 and partly due to a spring force exerted by the Bellville washers 260.

In one embodiment the channel 250 may be fabricated to increase friction for preventing slippage of the control link 112 within the channel when the aperture 242 is in the clamped state. For example, the channel 250 may be formed using carbide inserts within the longitudinal actuator 180 to increase the retaining force.

Figure 9:
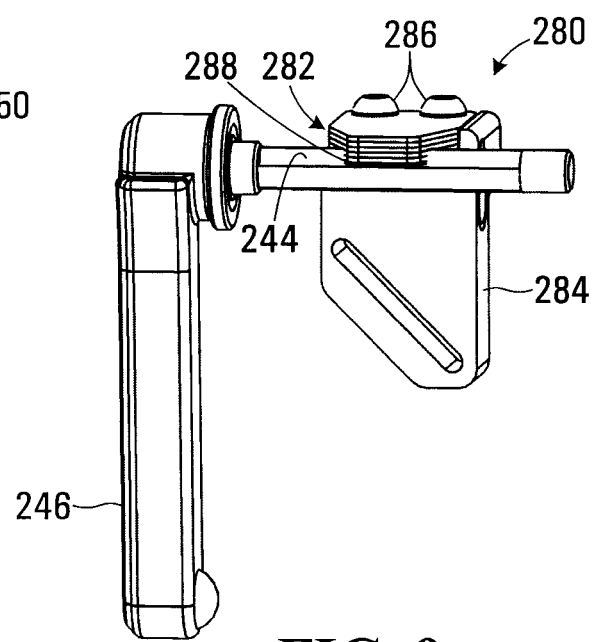
FIG. 9 is a side perspective view of an alternative embodiment of the longitudinal actuator.

Referring to FIG. 9 an alternative clamp plate embodiment is shown at 280. In this embodiment the clamp plate is provided by a stack of compliant clamp plates 282 mounted to a longitudinally moveable actuator 284. The stack of compliant clamp plates 280 are fastened to the longitudinal actuator 284 using a pair of screws 286 received in threaded holes (not shown) within the longitudinal actuator. A lower clamp plate 288 in the stack of compliant clamp plates 280 engages the eccentric pin 244 and the stack of plates operate together to provide the retaining force.

Figure 10:
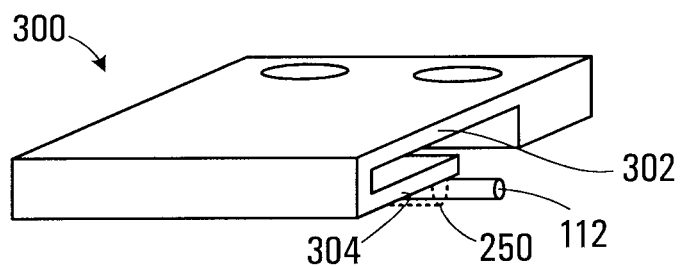
FIG. 10 is a perspective view of an alternative embodiment of a clamp plate for use in the longitudinal actuator shown in FIGS. 5-8.

Referring to FIG. 10, another alternative embodiment of the clamp plate is shown at 300. The clamp plate 300 has a first cantilevered length 302 that extends beyond the control link 112 in the channel 250 (shown in broken lines). The clamp plate 300 also has a second cantilevered length 304 in offset relation to the first cantilevered length 302 and extending back over the channel 250. The first and second cantilevered lengths 302 and 304 provide for a greater resilient deformation than the clamp plate 242 shown in the previously disclosed embodiments.

Referring back to FIG. 4, the clamp lever 246 is shown in the clamped position corresponding to the clamped state shown in FIG. 7 and the lever aligns with the back of the housing. When the lever 246 is opened to place the clamp aperture 240 in the open state (shown in FIG. 5), the lever will thus protrude from the actuator housing 102. When the surgical instrument 100 is received within a surgical system (not shown) the protruding lever may prevent loading of the surgical instrument while the clamp aperture 240 is open. This provides an additional level of safety that prevents an unclamped end effector 110 from being used in the surgical system, which could cause significant problems during a surgery.

The above disclosed embodiments provide for quick loading and unloading of the end effector 110 and thus facilitate use of different end effectors with the surgical instrument 100. The clamp aperture 240 thus facilitates quick loading of different end effectors into the surgical instrument 100. Additionally, the resiliently deformable clamp plate 242 permits the clamp aperture 240 to function over a fairly large tolerance band for clamping different end effectors.

The disclosed embodiments allow a disposable end effector 110 to be quickly and easily mounted on the surgical instrument 100. Typically the end effector 110 would be mounted on a sterilized instrument 100 prior to the commencement of the surgery. Once the surgery is completed the end effector 100 may be removed, which has the advantage of potentially reducing risk of infection since the contaminated end effector that was in contact with tissue during the procedure may be discarded. A new sterilized end effector 100 would then be used for the next procedure. The instrument 100 may be cleaned and sterilized for re-use, usually for a pre-determined number of uses. Removal of the end effector 110 prior to cleaning and sterilization simplifies cleaning of the surgical instrument 100 since there are less parts to clean and the bore 130 is open during cleaning for flushing out the any accumulated debris such as blood and tissue that may have accumulated during the procedure.

While specific embodiments have been described and illustrated, such embodiments should be considered illustrative of the invention only and not as limiting the invention as construed in accordance with the accompanying claims.

What is claimed is:

1. A surgical instrument apparatus for removably receiving an end effector coupled to an elongate control link for actuating the end effector to perform surgical operations, the apparatus comprising:
an actuator housing;
an elongate shaft extending from the actuator housing and including a bore for receiving the control link; and
an actuator mounted within the actuator housing and comprising a clamp aperture disposed to receive the control link while the clamp aperture is being urged into an unclamped state by an opening force, the clamp aperture being operably configured to move between the unclamped state and a clamped state in response to the opening force being released, the clamp aperture in the clamped state being operable to restrain the control link within the actuator for movement in a longitudinal direction substantially aligned with the elongate shaft, wherein the actuator includes:
a longitudinally moveable portion housing the clamp aperture;
a transversely movable portion for receiving a drive force; and
a coupling between the transversely moveable portion and the longitudinally moveable portion, the coupling being operable to convert transverse movement of the transversely moveable portion into longitudinal movement of the longitudinally moveable portion.

2. The apparatus of claim 1 wherein the clamp aperture comprises:
a channel for receiving the control link; and
a clamp plate disposed to engage and exert a clamping force on the control link when the clamp aperture is in the clamped state, the clamp plate being operable to resiliently deform in response to the opening force causing the clamp plate to disengage from the control link.

3. The apparatus of claim 2 wherein the clamp plate is mounted to the actuator at a location distal to the channel and comprises a cantilevered length extending over the channel, the cantilevered length of the clamp plate being configured to provide the resilient deformation.

4. The apparatus of claim 3 wherein the cantilevered length comprises:
a first cantilevered length extending beyond the channel; and
a second cantilevered length in offset relation to the first cantilevered length and extending back over the channel, the first and second cantilevered lengths configured to provide the resilient deformation.

5. The apparatus of claim 3 wherein the clamp plate is mounted to the actuator using a compliant mounting that permits further resilient deflection of the clamp plate about the compliant mounting.

6. The apparatus of claim 2 wherein the channel comprises a material treated to increase friction for preventing slippage of the control link within the channel when the aperture is in the clamped state.

7. The apparatus of claim 1 further comprising a clamp lever operable to provide the opening force when in an open position.

8. The apparatus of claim 7 wherein the clamp lever in the open position protrudes from the actuator housing and prevents loading of the surgical instrument into a driver for providing drive forces to the actuator when the clamp aperture is in an open state.

9. The apparatus of claim 1 further comprising:
a rotational actuator disposed within the actuator housing; and
a torque tube enclosing the elongate control link and extending through the bore of the elongate shaft, the torque tube being coupled to the rotational actuator and including a distal end operable to couple to the end effector for causing rotation of the end effector.

10. The apparatus of claim 9 wherein the rotational actuator comprises:
a rotatable portion coupled to the torque tube;
a transversely movable portion for receiving a drive force; and
a coupling between the transversely moveable portion and the rotatable portion, the coupling being operable to convert transverse movement of the transversely moveable portion into rotation of the rotatable portion and the torque tube.

11. A surgical instrument apparatus for removably receiving an end effector coupled to an elongate control link for actuating the end effector to perform surgical operations, the apparatus comprising:
an actuator housing;
an elongate shaft extending from the actuator housing and including a bore for receiving the control link; and
an actuator mounted within the actuator housing, the actuator including:
a longitudinally movable portion;
a clamp aperture disposed to receive the control link while the clamp aperture is being urged into an unclamped state by an opening force, the clamp aperture being operably configured to move between the unclamped state and a clamped state in response to the opening force being released, the clamp aperture in the clamped state being operable to restrain the control link within the actuator for movement in a longitudinal direction substantially aligned with the elongate shaft, wherein the clamp aperture is located within the longitudinally moveable portion of the actuator;
a transversely moveable portion; and
a linkage extending between the transversely moveable portion and the longitudinally moveable portion, the linkage being operably configured to translate transverse movement of the transversely moveable portion into longitudinal movement of the longitudinally moveable portion.

12. An end effector for use with the apparatus of claim 1, the control link of the end effector including an open end operably configured to be received and clamped within the clamp aperture.

* * * * *